(12) United States Patent
Don (10) Patent No.: US 7,223,246 B2
(45) Date of Patent: May 29, 2007

(54) DIAGNOSIS OF THE PRESENCE OF COCHLEAR HYDROPS USING OBSERVED AUDITORY BRAINSTEM RESPONSES

(75) Inventor: Manuel Don, Anaheim, CA (US)

(73) Assignee: House Ear Institute, Los Angeles, CA (US)

( * ) Notice: Subject to any disclaimer, the term of this patent is extended or adjusted under 35 U.S.C. 154(b) by 182 days.

(21) Appl. No.: 10/863,559

(22) Filed: Jun. 7, 2004

(65) Prior Publication Data

US 2005/0273018 A1    Dec. 8, 2005

Related U.S. Application Data

(60) Provisional application No. 60/520,856, filed on Nov. 17, 2003, provisional application No. 60/476,747, filed on Jun. 6, 2003.

(51) Int. Cl.
*A61B 5/00* (2006.01)
(52) U.S. Cl. .................................................. 600/559
(58) Field of Classification Search ............... 600/544, 600/545, 559
See application file for complete search history.

(56) References Cited

U.S. PATENT DOCUMENTS 6,080,112 A * 6/2000 Don .............................. 600/559
6,264,616 B1 * 7/2001 Don .............................. 600/559
2005/0137492 A1 * 6/2005 Eggermont et al. ......... 600/544

OTHER PUBLICATIONS

Gerull et al. Low-Frequency Masking of Brainstem Potentials. Scand Audiol 1991; 20: 227-234.*
Mrowinski et al. Diagnosis of Endolymphatic Hydrops by Low-Frequency Masking. Audiol Neurootol 1996; 1: 125-134.*

* cited by examiner

*Primary Examiner*—Max Hindenburg
*Assistant Examiner*—Michael Apanius
(74) *Attorney, Agent, or Firm*—Blakely, Sokoloff, Taylor & Zafman LLP (57) ABSTRACT

A procedure for diagnosing cochlear hydrops is based, in part, on an analysis of the patient's auditory brainstem response (ABR) to stimuli. The patient's ABR to a broadband click stimulus is recorded. A plurality of masked ABR's are also recorded, wherein the stimulus is masked by high-pass noise with a plurality of high-pass cut-off frequencies. The latency difference between the wave V component in the unmasked click alone response and the undermasked wave V component of a low cut-off frequency high-pass response is then calculated. If an undermasked component is not present, the normal wave V component is used. The measured latency difference is combined with another measure, such as the wave V amplitude ratio. A distribution of the combined measure is then plotted for the population and a threshold established for diagnosing cochlear hydrops. Alternatively, the joint distribution of the individual measures may be used in situations where the individual measures are known to be independent.

14 Claims, 7 Drawing Sheets

Wave V Latency Delay (500 Hz HP - Click Alone)

DIAGNOSIS OF THE PRESENCE OF COCHLEAR HYDROPS USING OBSERVED AUDITORY BRAINSTEM RESPONSES

RELATED APPLICATIONS

This invention claims priority of provisional application 60/476,747 filed Jun. 6, 2003 and of provisional application 60/520,856 filed Nov. 17, 2003.

This invention is related to the subject matter of U.S. Pat. Nos. 6,080,112 and 6,264,616. This invention is also related to the subject matter of application Ser. No. 10/818,806 filed Apr. 5, 2004. The disclosures of these patents and patent application are incorporated herein by reference.

This invention as made with government support under grants NIH NIDCD R01 DC 00043 and DC 003592 awarded by the National Institutes of Health. The government has certain rights in the invention.

BACKGROUND OF THE INVENTION

1. Field of the Invention

The subject invention provides an electrophysiological measure of the presence of cochlear hydrops in patients suspected of Meniere's disease.

2. Background

The major clinical diagnostic indicator of cochlear hydrops is hearing history. Cochlear hydrops is suspected if there is a fluctuating low-frequency hearing loss. Other popular older tests that have produced results of varying success are the glycerol test, the SP/AP (Summating Potential amplitude to compound Action Potential amplitude ratio) in electrocochleographic recordings, and, more recently, measures of cochlear traveling-wave velocities from derived-band Auditory Brainstem Responses (ABRs). Variations and combinations of these measures have also been investigated.

The disadvantages of the currently used diagnostic methods include:

(1) A fluctuating low-frequency hearing loss can occur in the absence of cochlear hydrops.

(2) The glycerol test is not an independent test because it must rely on another measure, (e.g., the SP/AP ratio) to determine if it is positive. Thus, the test is only as good as the second test used to measure the change that occurs due to administration of glycerol. Moreover, if the glycerol is administered orally, it is extremely unpleasant for the patient, and if administered intravenously it becomes an invasive procedure.

(3) The SP/AP ratio has been studied for a number of years and the results have varied greatly. Depending on the study, the sensitivity of the measure ranges from 50% and up. Other studies claim that the ratio change is due to changes in the AP value, whereas theoretically, changes due to cochlear hydrops should be in the SP value. While many studies can show a statistically significant difference for group or population data, the confidence of the diagnosis for a given individual is low due to overlap in the ratios for cochlear hydrops and non-hydrops populations. Moreover, the SP/AP ratio measures may require invasive transtympanic (needle through the eardrum) procedures for clear recordings. Even with transtympanic electrodes, due to the location of the recording electrode, these recordings are dominated by activity at the high-frequency end of the cochlea, whereas the diagnostic changes are more related to the low-frequency end of the cochlea.

(4) The cochlear traveling wave measures have not been studied extensively and their sensitivity and specificity are unknown at this time. Also, these measures have been shown to be highly variable across individuals because other factors unrelated to the presence of cochlear hydrops may affect these measures. We are currently investigating this measure in an NIH-funded grant project.

SUMMARY OF THE INVENTION

The present invention provides a procedure for diagnosing cochlear hydrops based, in part, on an analysis of the patient's auditory brainstem response (ABR) to stimuli. The patient's ABR to a broadband click stimulus is recorded. A plurality of masked ABR's are also recorded, wherein the stimulus is masked by high-pass noise with a plurality of high-pass cut-off frequencies. The latency difference between the wave V component in the unmasked click alone response and the undermasked wave V component of a low cut-off frequency high-pass response is then calculated. If an undermasked component is not present, the normal wave V component is used. The measured latency difference is combined with another measure, such as the wave V amplitude ratio. A distribution of the combined measure is then plotted for the population and a threshold established for diagnosing cochlear hydrops. Alternatively, the joint distribution of the individual measures may be used in situations where the individual measures are known to be independent.

DETAILED DESCRIPTION OF THE INVENTION

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

The derived-band ABR approach consists of the simultaneous ipsilateral presentation of a broad-band click and high-pass filtered pink noise. A series of responses are recorded as the cut-off frequency of the high-pass noise is successively lowered from one run to the next in one octave steps (8.0, 4.0, 2.0, 1.0, 0.5 kHz). Successive subtraction of these high-pass masked responses results in a series of derived-band ABRs representing activity initiated from regions of the cochlea approximately one octave wide. For adequate masking, the sound pressure level of the pink noise must be nearly equivalent to the peak equivalent sound pressure level of the click. For example, when using ER-2 insert earphones, the amount of pink noise required to mask an 82 dB p.e. SPL (peak-equivalent Sound Pressure Level) click is about 81 dB RMS SPL.

In work with patients diagnosed with Meniere's disease based on guidelines of the Committee on Hearing and Equilibrium (1994) that include symptoms consistent with the presence of cochlear hydrops, I have found that the amount of high-pass masking noise used to obtain the derived-band ABRs in normal-hearing and pure cochlear loss subjects, seems to be insufficient. This is demonstrated in FIGS. 1A-1B where a series of high-passed noise masked (not derived-band) responses are shown for a normal-hearing subject (FIG. 1A) and a patient diagnosed with Meniere's disease (FIG. 1B). Note that compared to the click alone and highest high-pass responses, the 500 Hz high-pass response is broader and the wave V latency is delayed in the normal-hearing subject. This is expected because most of the cochlea is masked and the response represents activity from below the 500 Hz region. For the Meniere's disease patient, wave V is not as broad and the latency is very short, comparable to the latency of wave V in the unmasked click alone and the higher high-pass responses. This is evidence that the activity from above the 500 Hz region has not been masked completely. Note that this "undermasking" effect is clearly seen in all of the Meniere's disease patient's lower high pass responses. The noise levels for these two cases were the same and were sufficient to mask normal-hearing and pure cochlear hearing loss individuals.

FIGS. 2A-2D illustrate ABRs for a patient diagnosed with Meniere's disease (with symptoms consistent with the presence of cochlear hydrops) in the left ear. The high-pass responses for the left ear (left panels) show the undermasking effect whereas the high-pass responses for the right ear (non-Meniere's non-cochlear hydrops) show the typical normal pattern. Note the large and sharp wave V amplitude of the sum of the five high-pass responses for the left ear diagnosed as having Meniere's disease (heavy trace in FIG. 2A). In comparison, the wave V of the sum of the high-pass responses for the right ear without Meniere's disease (heavy trace in FIG. 2C) is broad and its amplitude is relatively small. In this patient, the amplitude ratio of the sum of the five high-pass noise masked responses to five times the unmasked click alone wave V amplitude is 0.903 for the Meniere's ear and 0.402 for the non-Meniere's ear.

Figure 2A:
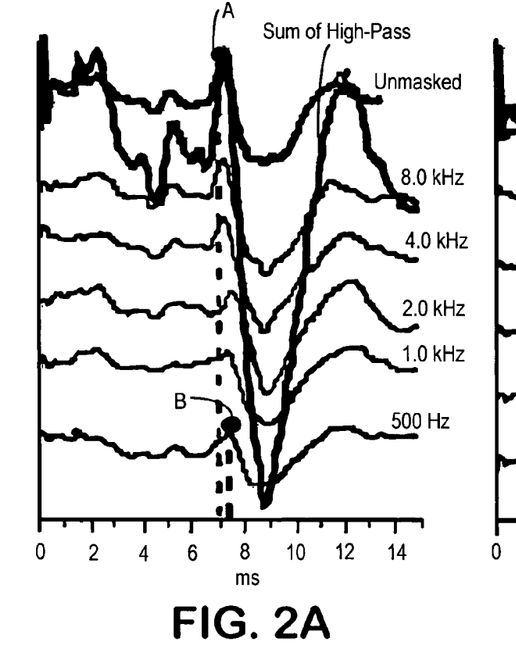
FIGS. 2A-2D illustrate derived-band ABRs for a unilateral Meniere's disease patient.
Figure 2B:
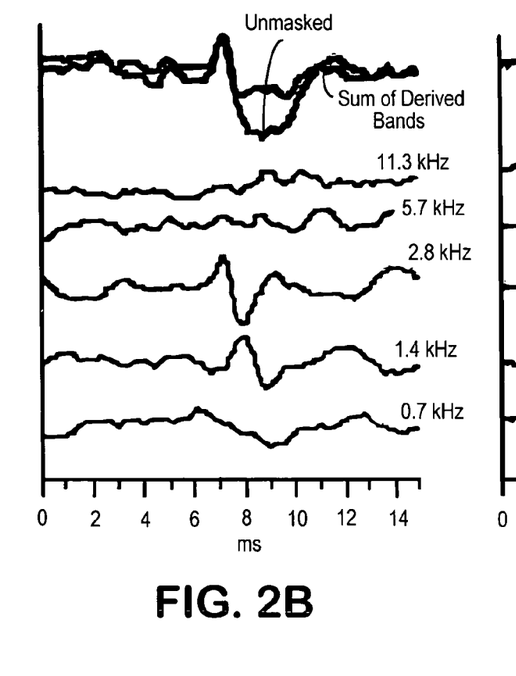
Figure 2C:
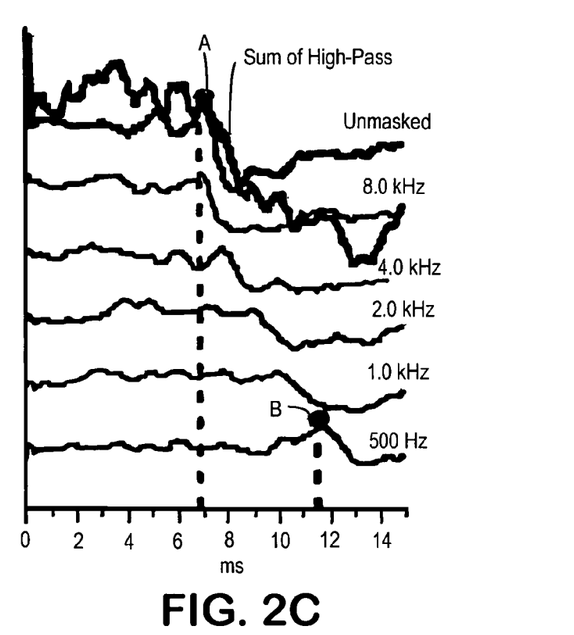

Also note that the latency delay between wave V of the unmasked click alone (point A) and wave V of the 500 Hz high-pass (point B) is minimal (less than 0.2 ms) for the ear with Meniere's disease (FIG. 2A) and rather long (over 4 ms) in the ear without Meniere's disease (FIG. 2C). Even in non-Meniere's subjects there can be an undermasked component, but its latency will still be longer than that seen in Meniere's disease ears with cochlear hydrops.

Figure 2D:
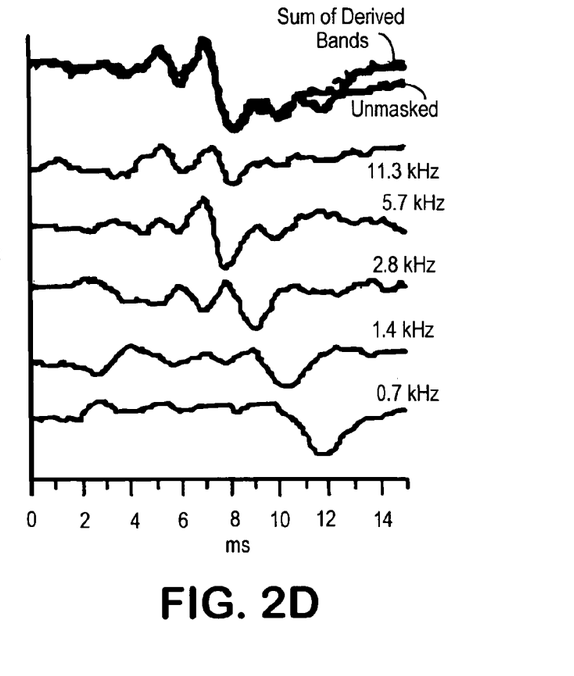
Figure 3A:
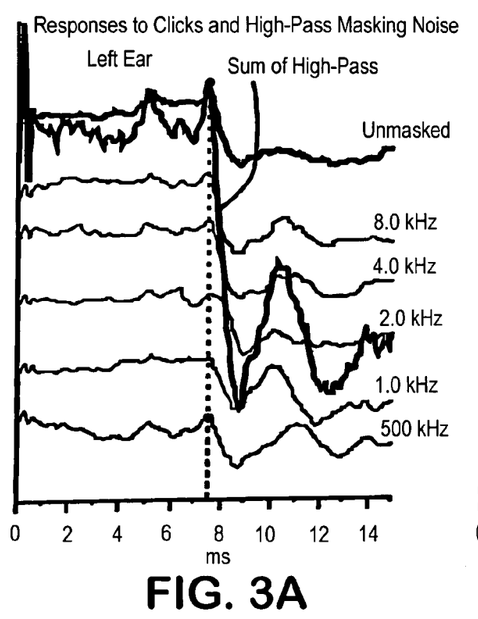
FIGS. 3A-3D illustrate derived-band ABRs for a bilateral Meniere's disease patient.
Figure 3B:
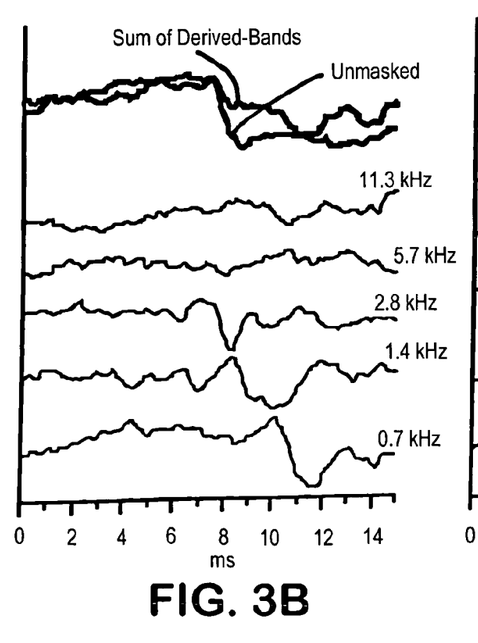
Figure 3C:
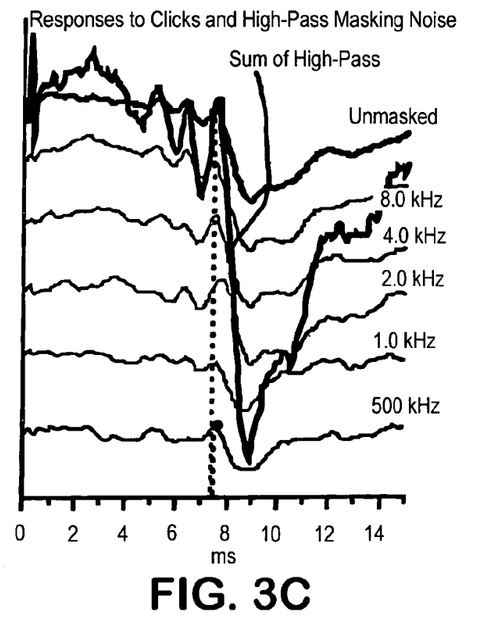
Figure 3D:
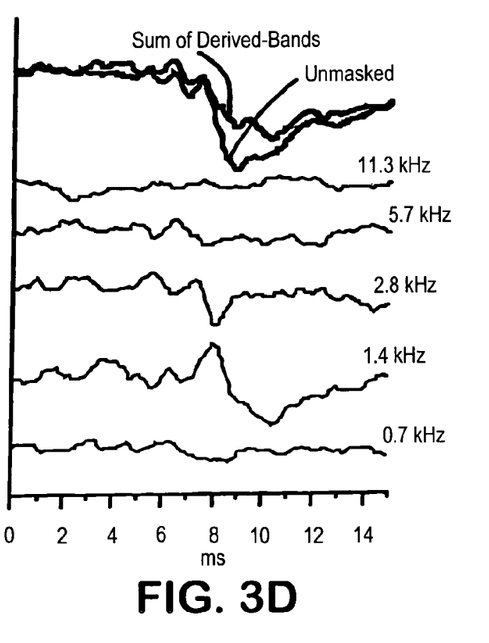

FIGS. 2B and 2D compare the sum of the derived-band response to the click alone response for the ear with Meniere's and the non-Meniere's ear respectively. For the Meniere's ear, the sum is much smaller than the click alone response, whereas for the non-Meniere's ear, the sum is essentially equivalent to the click alone response.

FIGS. 3A-3D illustrate an example of a patient diagnosed with bilateral Meniere's disease and cochlear hydrops. The undermasking pattern is evident for both ears. I hypothesize that this greater resistance to masking is a consequence of the changes in the mechanical properties of the basilar membrane induced by pressure exerted by the endolymphatic (cochlear) hydrops condition.

Figure 1A:
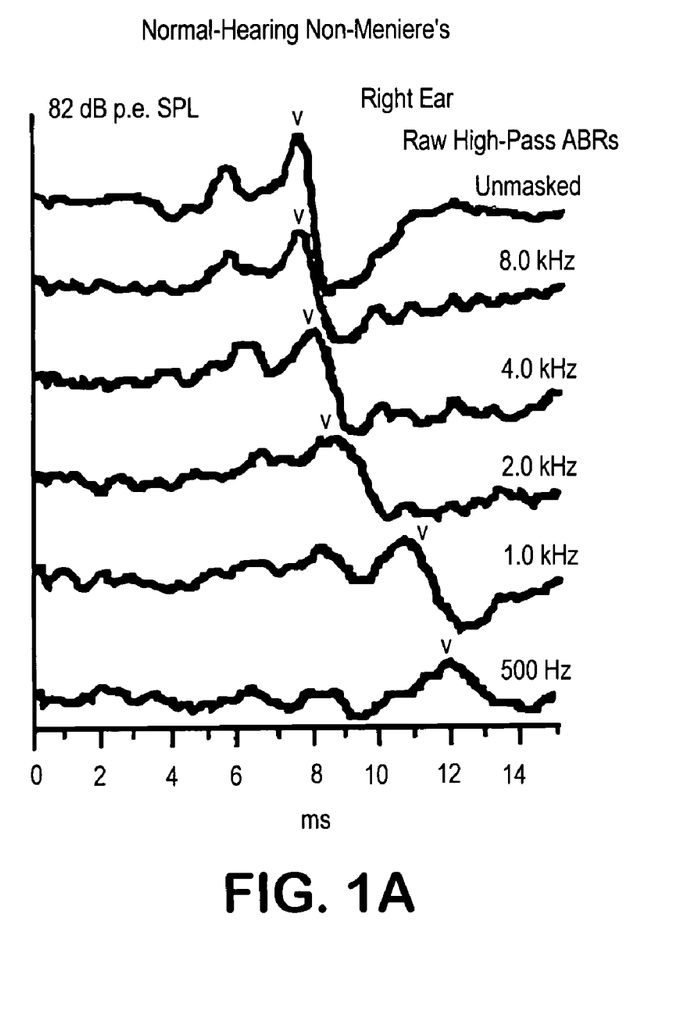
FIGS. 1A-1B illustrate derived-band ABRs for patients with normal hearing and Meniere's disease.
Figure 1B:
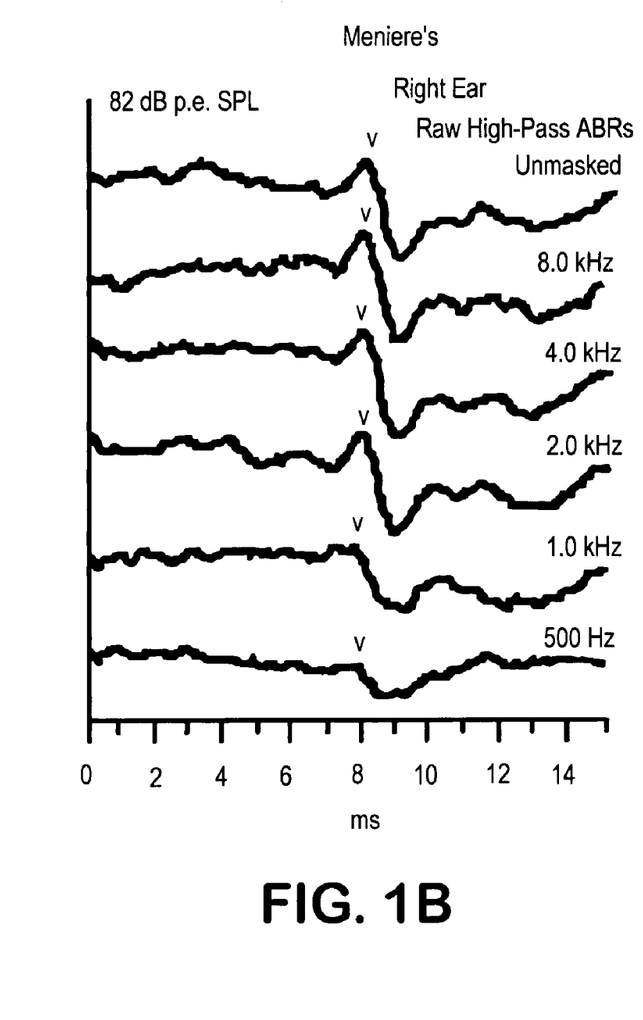

While visual recognition of the undermasking is obvious as seen in FIGS. 1-3, objective latency and amplitude measures of the high-pass noise masking ABR responses, amplitudes of sums of high-pass ABR and derived-band responses, as well as cross-correlation measures between these various waveforms, can be used for the assessment of cochlear hydrops. Some useful measures or variants of these measures are: (1) the wave V amplitude ratio of the sum of the five high-pass masking responses (large heavy traces in FIG. 2) to five times the unmasked click alone response, (2) the cross correlation between the response to the 500 Hz high-pass condition and the unmasked click alone response, (3) the latency difference between wave V of the unmasked click alone response and wave V of the 500 Hz high-pass response as determined by visual peak selection or by analyses of the peak in the cross-correlation function, and (4) the amplitude difference between the unmasked click alone response and the sum of the five derived-band responses.

The presently preferred measure is measure (3) noted above. However, there is a problem in that there are two possible wave V peaks in the 500 Hz high-pass response that are not always present together. We have labeled the early latency wave V peak as the undermasked wave V component. If this peak occurs, we use this early component in our measure. If it does not exist, then we use the longer latency normal wave V peak. In either case, the latency difference between the unmasked click alone response and the 500 Hz high-pass masked response is shorter in the Meniere's disease ears than in the non-Meniere's disease ears.

Figure 4A:
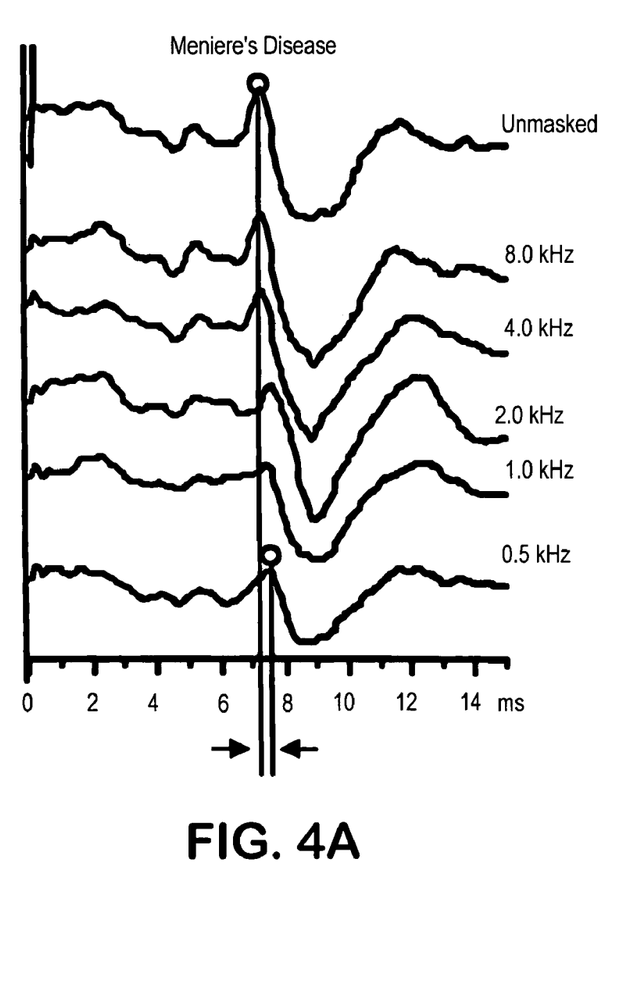
FIGS. 4A-4B illustrate undermasking in a Meniere's disease ear vs. a normal ear.
Figure 4B:
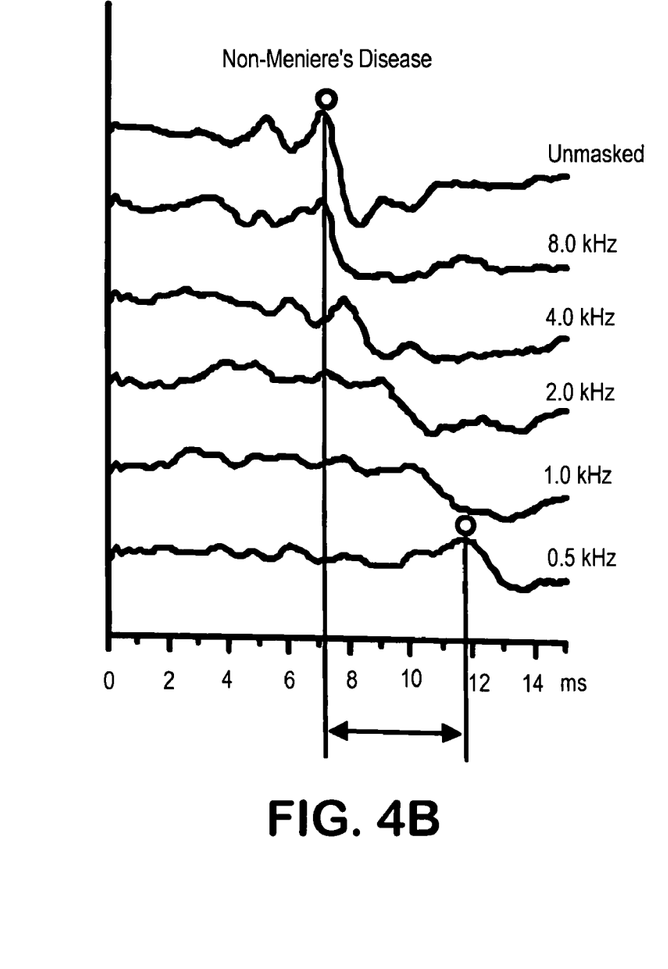

FIGS. 4A-4B illustrate the undermasking phenomenon as evidenced by the latency delay between wave V in the unmasked click alone response and wave V in the 500 Hz high-pass response. FIG. 4B presents the responses from a non-Meniere's disease ear. We determine the latency of wave V in the 500 Hz high-pass response, then the latency of wave V in the unmasked click alone response, and subtract the two to find the delay. We can then compare this delay to the delay we find in a Meniere's disease ear as shown in FIG. 4A. As is apparent, the latency delay is much shorter in the Meniere's disease ear.

Figure 5:
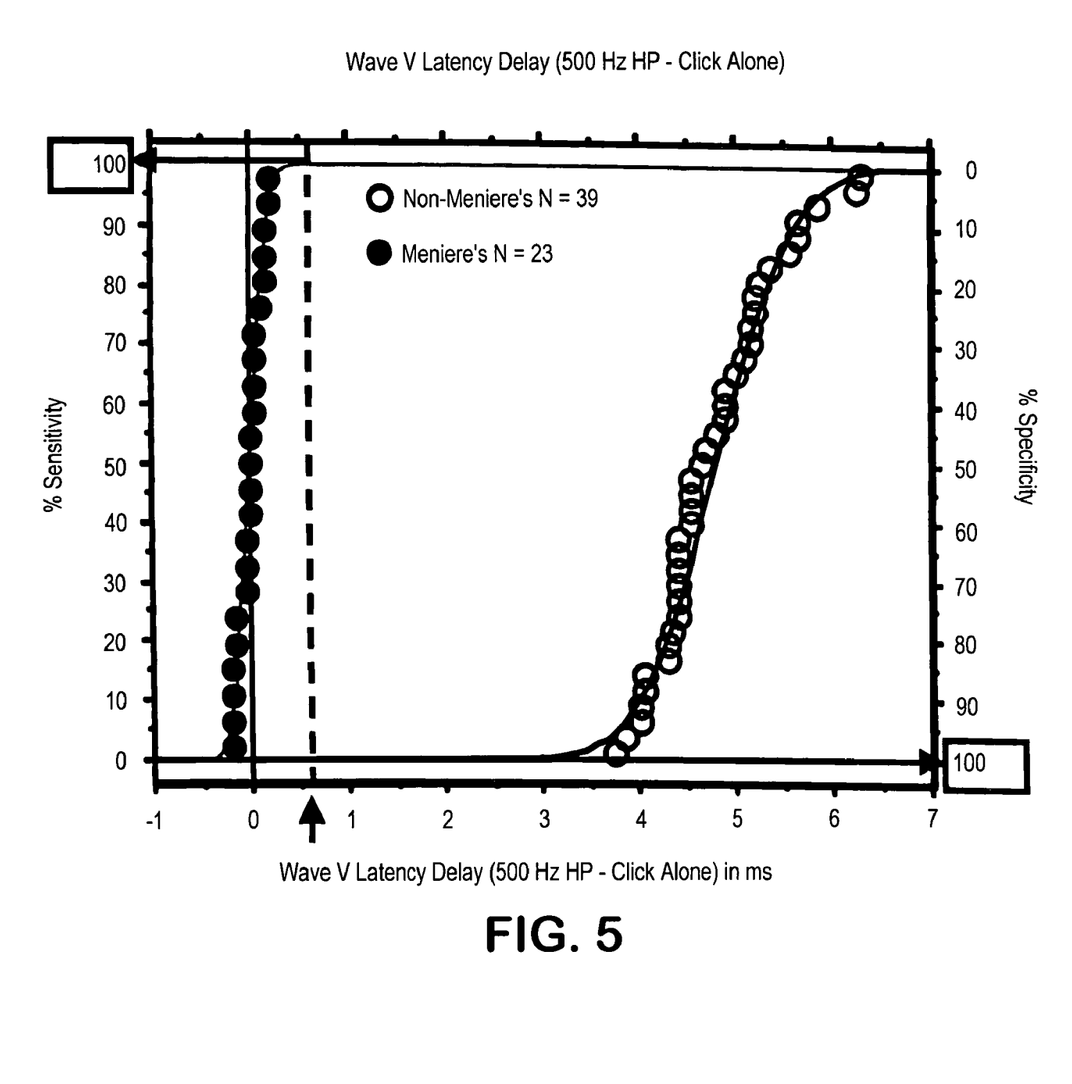
FIG. 5 compares wave V latency delay of an unmasked response between a population with normal hearing and a population with Meniere's disease.

FIG. 5 illustrates the results from 39 normal-hearing non-Meniere's disease ears and 20 Meniere's disease ears. In this figure, the latency delay between wave V of the click alone response and wave V of the 500 Hz high-pass response is plotted on the x-axis and the cumulative percent is plotted on the y-axis. Given the greater degree of undermasking observed in Meniere's disease with cochlear hydrops, the wave V latency delay for the Meniere's disease ears is less than that for the non-Meniere's disease ears. Note the total separation between the distributions for the two populations tested: normal-hearing, non-Meniere's disease subjects and patients with Meniere's disease. All of the Meniere's disease results (filled circles) fall well below 0.6 ms (see arrow and dotted line) while all the normal-hearing, non-Meniere's disease results (open circles) fall well above 0.6 ms. So if we set our test criterion at 0.6 ms, we get 100% sensitivity and 100% specificity for these two populations.

Figure 6A:
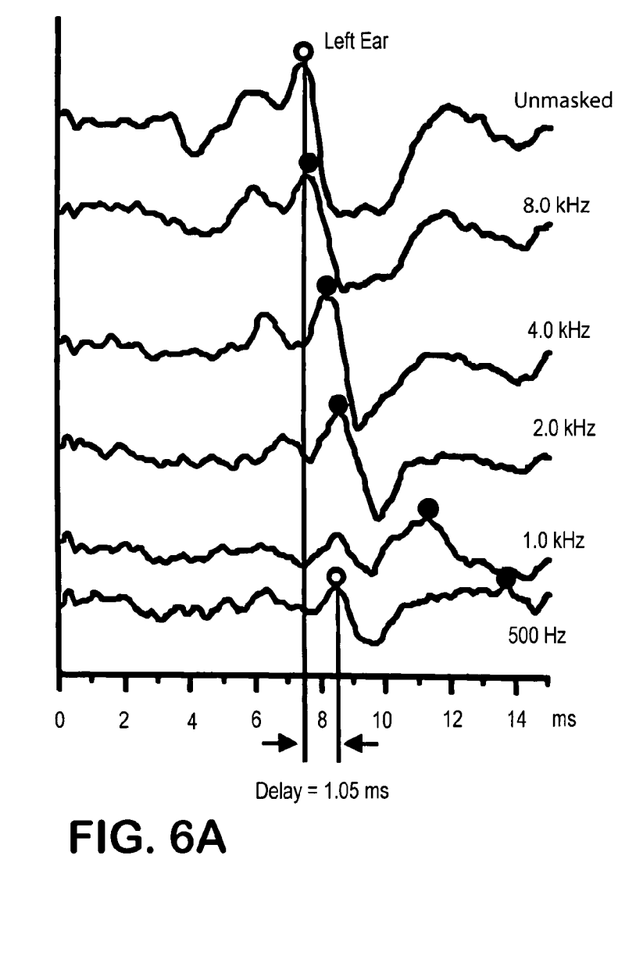
FIGS. 6A-6B illustrate undermasking in a patient with normal hearing.
Figure 6B:
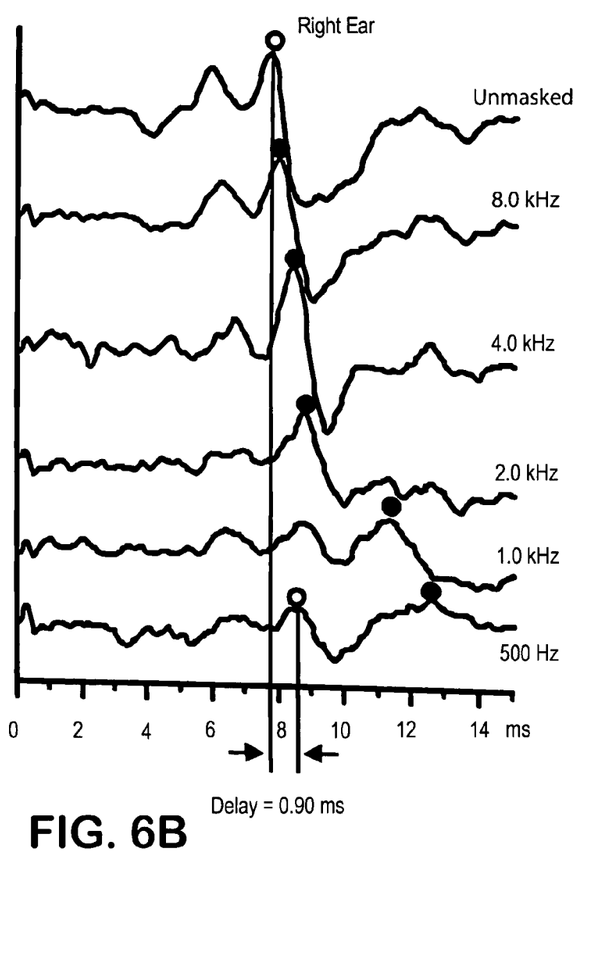

FIGS. 6A-6B present the responses from a normal-hearing, non-pathologic subject. An experienced analyst can see wave V (filled circles) moving out in time, just as it should in a non-Meniere's disease ear. But even for a well trained analyst, the peak of wave V on the 500 Hz response may be difficult to distinguish. In fact, if we look more closely at the 500 Hz high-pass response, we can see a peak in the response for each of the subject's ears that is only slightly delayed from the peak of wave V in the unmasked click alone response (open circles). Remember that the level of masking chosen was based on an average. This means that for some non-pathologic ears, the masking won't be enough and we'll see a peak in the 500 Hz high-pass response due to unmasked activity in the higher frequencies. This is what we call the undermasked wave V component of the response. If we use a latency delay of $\leq 0.6$ ms as the criterion for Meniere's disease, note that even a mistaken choice of the undermasked peak in the response as wave V of the 500 Hz high-pass response will provide the correct diagnosis.

Figure 7:
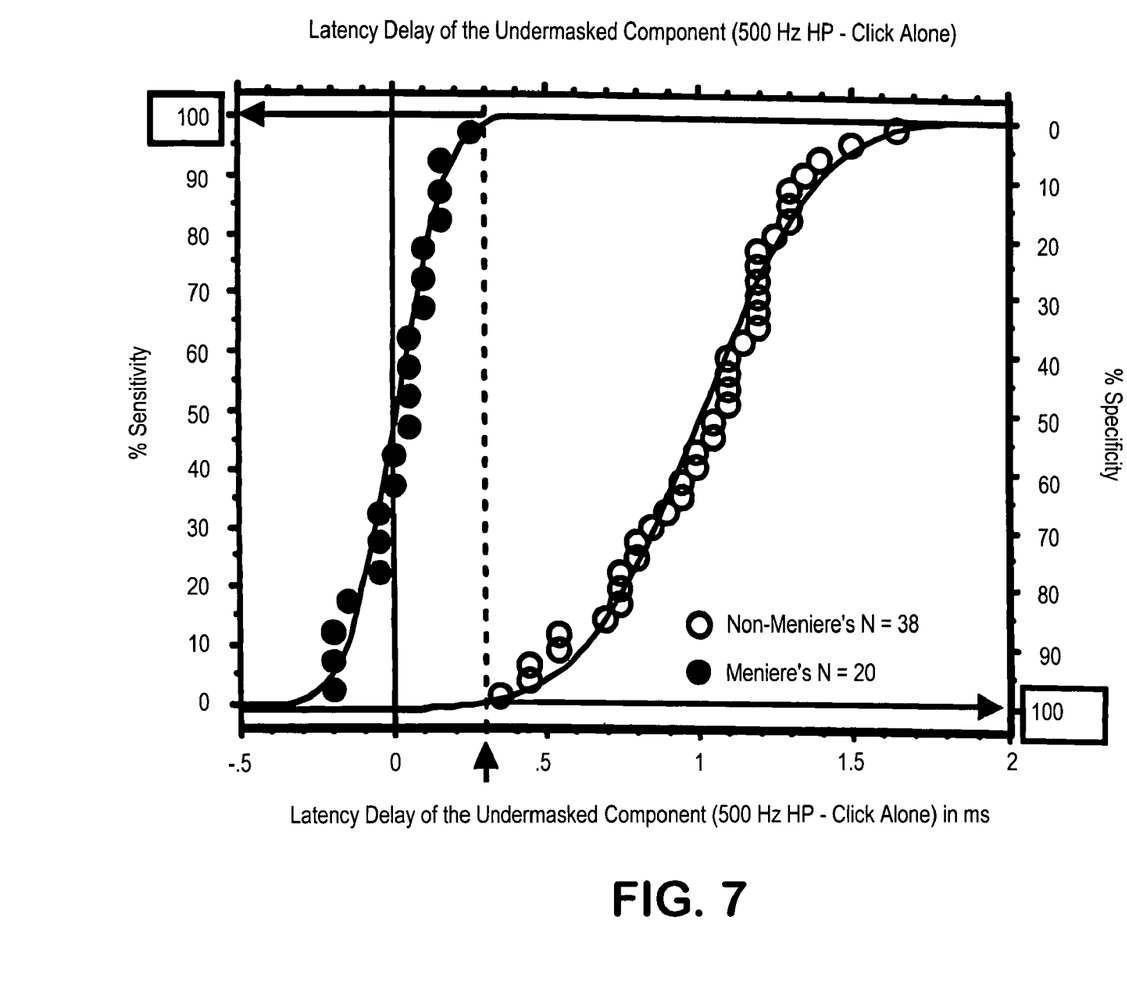
FIG. 7 compares wave V latency delay of an undermasked component between a population with normal hearing and a population with Meniere's disease.

FIG. 7 illustrates the results from 38 normal-hearing non-Meniere's disease ears and 20 Meniere's disease ears. In this figure, the latency delay between wave V of the click alone response and the undermasked component of the 500 Hz high-pass response is plotted on the x-axis and the cumulative percent is plotted on the y-axis. As for the wave V latency delay just described, due to the greater degree of undermasking observed in Meniere's disease with cochlear hydrops, the latency delay of the undermasked component for the Meniere's disease ears is less than that for the non-Meniere's disease ears. Although these two distributions are closer together compared to the distributions for the masked wave V latency delay in FIG. 5, there is still a total separation between the non-Meniere's disease and Meniere's disease results. All of the Meniere's disease results fall below 0.3 ms while all the non-Meniere's disease results fall above 0.3 ms. So if we set our test criterion at 0.3 ms, we still get 100% sensitivity and 100% specificity for these two populations.

The following are some other measures being examined that may be considered variants of the four measures enumerated above:

(a) The amplitude of wave V when the 500 Hz high-pass response is subtracted from the unmasked click alone response, then this amplitude is divided by the amplitude of the unmasked click alone response. Subtracting the 500 Hz high-pass response from the unmasked click alone response is mathematically identical to the sum of the five derived-band responses noted in measure (4) above. Instead of looking at the amplitude difference noted in measure (4), we are taking a ratio of these amplitudes.

(b) The ratio measure in (a) is multiplied by measure (3) above. The latency difference between wave V of the unmasked click alone response and the undermasked component of the 500 Hz high-pass response is used, if present. If the undermasked component is not present in the 500 Hz high-pass response, then the normal high-pass wave V is used. To avoid possible negative numbers in cases where the latency of the 500 Hz high-pass undermasked component is shorter than that of wave V in the unmasked click alone response, a constant (e.g., 1) is added to the latency difference before multiplying by the ratio.

(c) The ratio of the wave V amplitude of the undermasked component (if present) in the 500 Hz high-pass response to that of the unmasked click alone response.

The latency, amplitude and correlation measures described above are to be used to assess the presence of cochlear hydrops in patients suspected of having Meniere's disease.

However, because of similar clinical symptoms, there is often a need to first rule out the presence of an acoustic tumor. Use of the Stacked ABR methodology for acoustic tumor evaluation is the subject of U.S. Pat. Nos. 6,080,112 and 6,264,616. This methodology uses the Stacked ABR amplitude measure to assess the presence of an acoustic tumor. To form the Stacked ABR, responses to clicks in the presence of high-pass masking noise at various cutoff frequencies must be collected. These responses are then successively subtracted to form derived-band responses that are then shifted and added together to form the Stacked ABR. To detect cochlear hydrops and Meniere's disease, the measures described above evaluate the degree of undermasking in the responses to the high-pass masking noise. Thus, while the measures for these two pathologies focus on different responses, the same set of data can be used for the assessment of both pathologies. That is, no additional data collection is required.

Preliminary data suggest that there is very little overlap between non-Meniere's disease patients and patients who have been diagnosed with Meniere's disease on the basis of the stringent guidelines of the Committee on Hearing and Equilibrium (1994). Thus, measured values exceeding, for example, two standard deviations of non-Meniere's, normal-hearing individuals could be diagnostic for cochlear hydrops and Meniere's disease.

This invention will provide a possible way to assess the presence of cochlear hydrops that is much easier for the clinician to use consistently, efficiently, and, most importantly, correctly in the diagnosis of Meniere's disease. The advantages of the measures in this invention are (1) it is a non-invasive procedure, (2) it is a relatively comfortable procedure, (3) it may be more sensitive in detecting the presence of cochlear hydrops, (4) it is relatively rapid and inexpensive.

It will be recognized that the above-described invention may be embodied in other specific forms without departing from the spirit or essential characteristics of the disclosure. Thus, it is understood that the invention is not to be limited by the foregoing illustrative details, but rather is to be defined by the appended claims.

What is claimed is:

1. A procedure for diagnosing cochlear hydrops comprising:
   recording a patient's auditory brainstem response to an unmasked broadband click stimulus;
   recording a plurality of masked auditory brainstem responses, wherein each of the masked auditory brainstem responses is responsive to a broadband click stimulus that is masked by high-pass noise with a high-pass cut-off at a respective one of a plurality of cut-off frequencies;
   calculating a latency difference between a wave V peak of the unmasked response and a wave V peak of a masked response having a low cut-off frequency;
   diagnosing the likely presence of cochlear hydrops if the latency difference is less than a threshold value based on results in an appropriate control population.

2. The procedure of claim 1 wherein the wave V peak of the masked response having a low cut-off frequency is an undermasked wave V component.

3. The procedure of claim 1 wherein the plurality of cut-off frequencies comprise 8 kHz, 4 kHz, 2 kHz, 1 kHz and 500 Hz.

4. The procedure of claim 1 wherein the low cut-off frequency is a lowest of the plurality of cut-off frequencies.

5. The procedure of claim 1 wherein the low cut-off frequency is 500 Hz.

6. The procedure of claim 1 wherein the latency difference is combined with another measure of cochlear hydrops to diagnose the likely presence of cochlear hydrops.

7. The procedure of claim 6 wherein the other measure of cochlear hydrops comprises a ratio of a sum of wave V peak amplitudes of the plurality of masked responses to a wave V peak amplitude of the unmasked response.

8. The procedure of claim 6 wherein the other measure of cochlear hydrops comprises a cross correlation between the masked response having a low cut-off frequency and the unmasked response.

9. The procedure of claim 6 wherein the other measure of cochlear hydrops comprises an amplitude difference between the unmasked response and a sum of the masked responses.

10. The procedure of claim 6 wherein the other measure of cochlear hydrops comprises a ratio of the difference between a wave V peak amplitude of the unmasked response and a wave V peak amplitude of the masked response having a low cut-off frequency to the wave V peak amplitude of the unmasked response.

11. The procedure of claim 6 wherein the other measure of cochlear hydrops comprises a product of:
   a ratio of the difference between a wave V peak amplitude of the unmasked response and a wave V peak amplitude of the masked response having a low cut-off frequency to the wave V peak amplitude for the unmasked response multiplied by
   a latency difference between the wave V peak of the unmasked response and a wave V peak of a masked response having a low cut-off frequency.

12. The procedure of claim 11 wherein the wave V peak of the masked response having a low cut-off frequency is an undermasked wave V component.

13. The procedure of claim 6 wherein the other measure of cochlear hydrops comprises a ratio of a wave V peak amplitude of the masked response having a low cut-off frequency to a wave V peak amplitude of the unmasked response.

14. The procedure of claim 13 wherein the wave V peak of the masked response having a low cut-off frequency is an undermasked wave V component.

* * * * *